United States Patent [19]

Kalopissis et al.

[11] 4,010,200

[45] Mar. 1, 1977

[54] N,N-DIARYL ALKYLENEDIAMINE OXIDATION DYE COMPOUNDS

[75] Inventors: Gregoire Kalopissis, Paris; Andree Bugaut, Boulogne-sur-Seine, both of France

[73] Assignee: Societe Anonyme dite: L'Oreal, Paris, France

[22] Filed: Dec. 5, 1974

[21] Appl. No.: 529,922

Related U.S. Application Data

[60] Continuation of Ser. No. 277,035, Aug. 1, 1972, abandoned, which is a division of Ser. No. 846,577, July 31, 1969, Pat. No. 3,694,138.

[30] Foreign Application Priority Data

Aug. 2, 1968 Luxembourg .......................... 56631

[52] U.S. Cl. ........................... 260/570.5 P; 8/10.2; 8/11; 260/556 AR; 260/562 R
[51] Int. Cl.$^2$ ......................................... C07C 91/28
[58] Field of Search ............................. 260/570.5 P

[56] References Cited

UNITED STATES PATENTS 2,661,291  12/1953  Slifkin .......................... 260/570.5 X

*Primary Examiner*—Robert V. Hines
*Attorney, Agent, or Firm*—Cushman, Darby & Cushman

[57] ABSTRACT

N,N'-diaryl alkylene diamine oxidation dye compounds that are suitable for dyeing live human hair.

6 Claims, No Drawings

N,N-DIARYL ALKYLENEDIAMINE OXIDATION DYE COMPOUNDS

This is a continuation of application Ser. No. 277,035 filed Aug. 1, 1972 and now abandoned, which is a division of Ser. No. 846,577 filed July 31, 1969, now U.S. Pat. No. 3,694,138.

SUMMARY OF THE INVENTION

It is well known that keratinic fibers, and in particular human hair, may be colored by compositions containing oxidation dyes, and in particular aromatic ortho or paradiamines and ortho or para-aminophenois which are generally referred to as "oxidation bases". These bases are capable of forming pigments as a consequence of oxidative coupling either between themselves or with color modifiers or couplers which may be, in particular, aromatic metadiamines or meta-aminophenois.

The present invention relates to a new class of bases which may be used for dyeing keratinic fibers.

It is the object of the present invention to provide as a new article of manufacture a dyeing composition for keratinic fibers, and particularly for human hair, which is characterized by the fact that it contains, possibly in association with one or more couplers, at least one base having the following general formula:

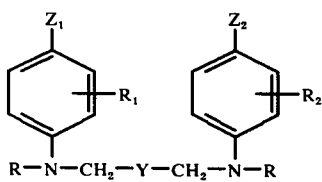

in which:

$Z_1$ and $Z_2$, which may be identical or different, represent hydroxyl or $NHR_3$, in which $R_3$ represents hydrogen or a lower alkyl having 1–6 carbon atoms;

$R_1$ and $R_2$, which may be identical or different, each represent hydrogen, halogen or alkyl;

R represents hydrogen, alkyl, hydroxyalkyl or aminoalkyl in which the amine constituent may be substituted;

Y represents a member selected from the group consisting of the following:

—(CH₂)ₙ—

(CH₂)n′—O—(CH₂)n′—

—(CH₂)n′—CHOH—(CH₂)n′— and

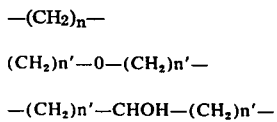

and $n$ is a whole number between 0 and 8 inclusive and $n'$ is a whole number between 0 and 4 inclusive.

It will be appreciated that the compounds of formula I may be used in the form of their acid addition salts.

Among the bases having general formula I which are particularly useful are:

N,N′bis-[(4-amino)phenyl]-tetramethylene diamine

N,N′bis(β-diethylaminoethyl) N,′-[(4-amino)phenyl]-tetramethylene diamine and

N-(4-hydroxy)phenyl N′-[(4′-amino)phenyl]-ethylene diamine

Among the couplers which may be advantageously used with the bases responding to formula I are:
meta-aminophenol,
meta-phenylene diamine,
meta-diamino-anisole,
2,4-dichloro-α-napththol
3-carbamyl-methyl-amino-6-methyl-phenol and
3-carbamyl-methyl-amino-phenol.

The concentration of the formula I base in the hair dyeing compositions according to the invention is betwen 0.15 and 12% by weight.

When couplers are used in association with the bases according to formula I the ratio of the concentration of the base to that of the coupler may vary within broad limits but an excess of coupler is preferably used.

The coloring compositions according to the invention may contain other dyes which may be used under the same conditions such as direct dyes, for example, azo or anthraquinone dyes, or dyes obtained by the oxidation of other bases than those listed above. These bases may be used in association with couplers.

The compositions according to the invention may also contain wetting agents, dispersing agents, penetrating agents, and any other ingredients conventionally used in dyeing hair. They may take the form of an aqueous solution, a cream or a gel.

The coloring compositions of this invention are generally used in a conventional manner at an alkaline pH, preferably between 8 and 10, and are applied to the hair in the presence of an oxidizing solution that may be used on the hair and which is preferably a solution of hydrogen peroxide.

It is also an object of the present invention to provide a method of coloring hair which is characterized by the fact that, after having added hydrogen peroxide thereto, a coloring composition such as the one defined above is applied to the hair. This composition is rendered alkaline by adding for example ammonia, before it is applied to the hair. The hair is then rinsed, shampooed and dried.

A further object of the present invention is to provide a method of preparing symmetrical N,N′-diaryl-α,ω-alkylene-diamines having the formula:

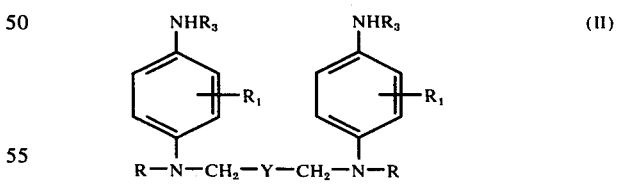

The first step of this process is to condense, preferably in a dimethylformamide medium, a dihalogeno-hydrocarbon having the formula X — CH₂ — Y — CH₂ — X (in which X indicates a halogen atom) on an alkaline or alkaline earth salt of an N-acetyl N′-arylsulfonyl paraphenylene diamine having formula A, which produces a compound B, which may then be totally hydrolyzed in a second step, using hot hydrochloric acid, when it is desired to obtain a compound in which R is a hydrogen atom, that is to say having formula III. When it is desired to obtain a compound in which R is not a hydrogen atom, compound B is first subjected to a selective hydrolysis of its aryl-sulfonyl groups, using cold sulfuric acid, after which the compound C thus obtained is reacted with a compound R'X (in which X designates a halogen and R' has the significance given for the radical R, except for hydrogen) so as to obtain a compound D which is deacetylated by hydrolysis with hot hydrochloric acid. This yields a compound having formula IV. This group of reaction is diagrammatically represented below.

formed by $R_1$ and $R_2$, on the one hand, and $Z_1$ and $Z_2$, on the other hand, comprises different radicals. In this process:

1. When $Z_1$ = OH and $Z_2$ = $NHR_3$, a para chloronitrobenzene having formula E set forth below is condensed in a first step on a para-[N-(ω-aminoalkyl)]-amino anisole having formula F. The product G which is obtained in this manner is then subjected to conventional reduction of the $NO_2$ group (for example by means for tin in a hydrochloric medium). This leads to a com-

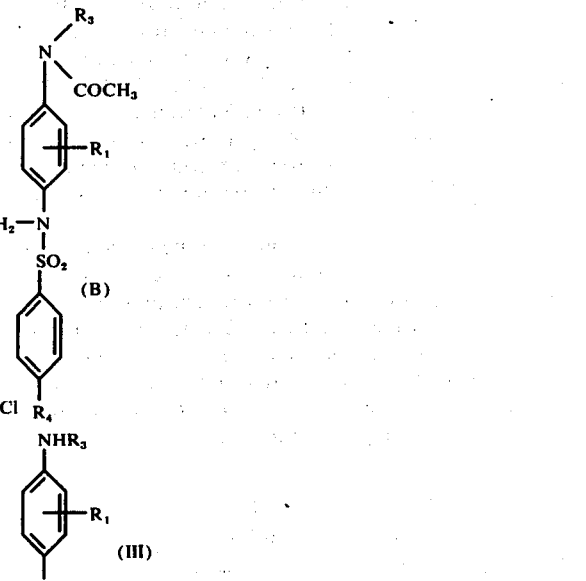

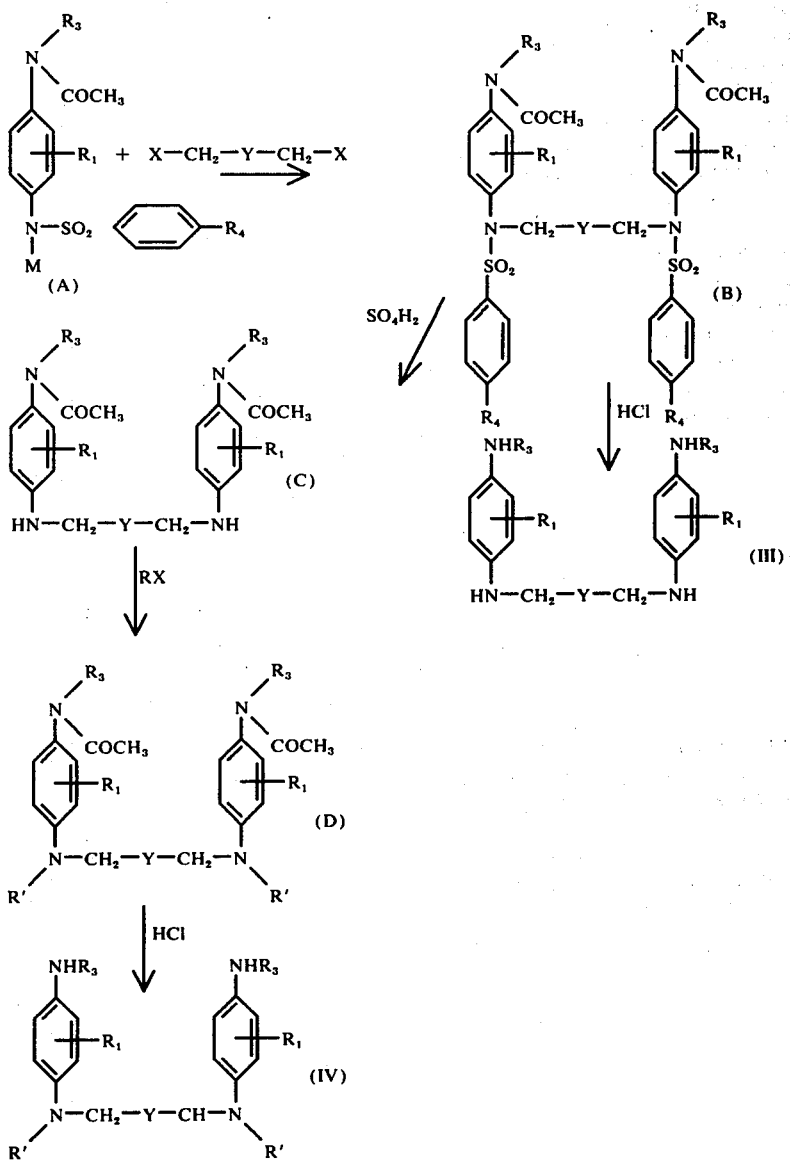

In the formulas shown thereon $R_1$, $R_3$, and Y have the significance given for the compounds of formula I, M represents an alkaline, such as Na, K or Li, or alkaline earth metal, such as Mg, Ca or Ba, R' designates an alkyl, hydroxy alkyl or amino alkyl group which may be substituted at the nitrogen, and $R_4$ represents either hydrogen or a methyl or nitro group.

Yet another object of the invention is to provide a new method of preparing compounds having formula I in which the molecule asymmetric, that is to say in which at least one of the two groups of substituents pound H which may then be directly treated with hydrobromic acid when a compound V which has a primary amine function is to be obtained. If such is not the case, the compound H is first treated with a halogenated derivative R''$_3$X (in which R''$_3$ designates a lower alkyl and X represents a halogen), before liberating the phenol function by using hydrobromic acid.

This produces a compound V'. This group of reactions is illustrated in the table below in which R'' represents a hydrogen atom or an alkyl radical, while $R_1$, $R_2$ and Y have the significances indicated for the compounds of formula I:

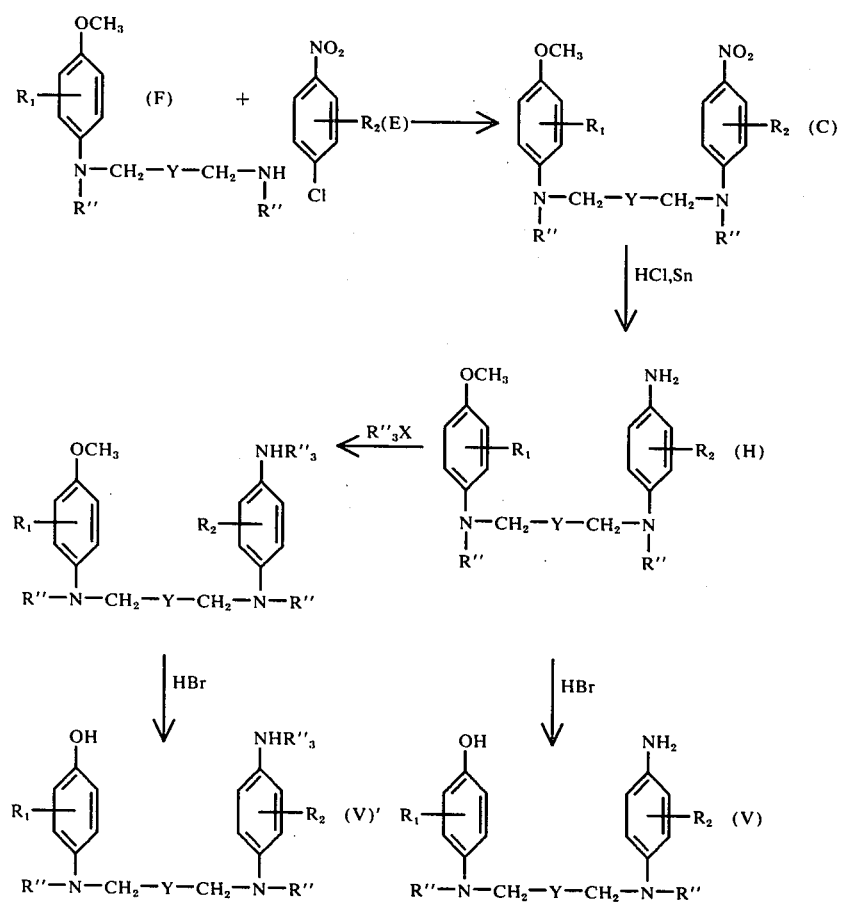

2. When $Z_1$ and $Z_2$ represent two amino groups which may be identical or different, which situation may be represented by $Z_1 = NHR_3$ and $Z_2 = NHR'_3$, a compound having the formula J (obtained in accordance with the process described in Luxembourg application No. 49,213 of July 30, 1965) is condensed, preferably in a dimethyl formamide medium, on a compound having formula K, after which the resulting compound L may be subjected to complete hydrolysis with hot hydrochloric acid if its is desired to obtain a compound in which $R = H$. Alternatively, the compound L may be subjected to selective hydrolysis with sulfuric acid, which produces a compound M, which may then be reacted with a halogenated derivative R'X. The resulting compound N when subjected to hydrolysis with hydrochloric acid yields a compound VII. This group of reactions is illustrated in the table below, in which $R'_3$ represents hydrogen or lower alkyl, while $R_1$, $R_2$, $R_4$, R', Y, X and M have the significance hereinbefore indicated.

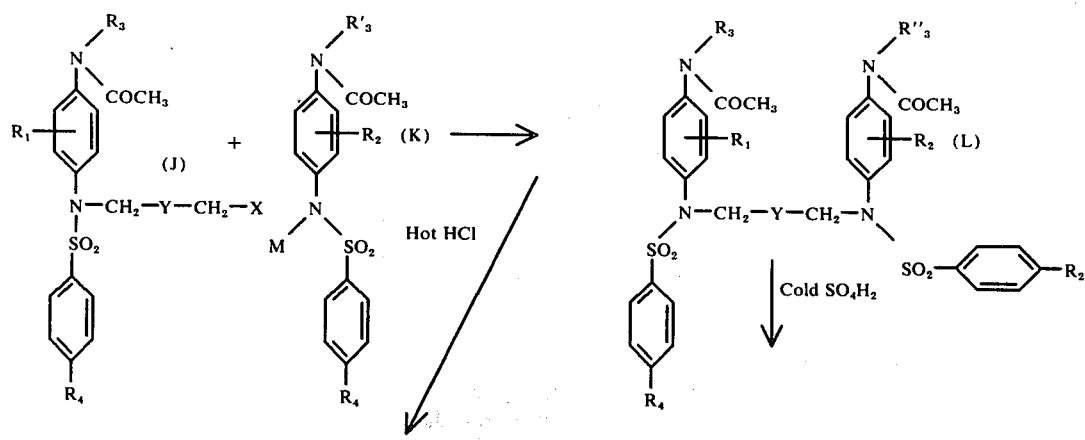

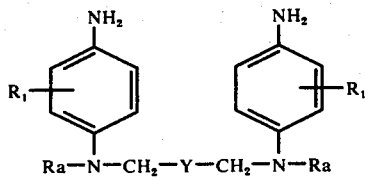

(VI)

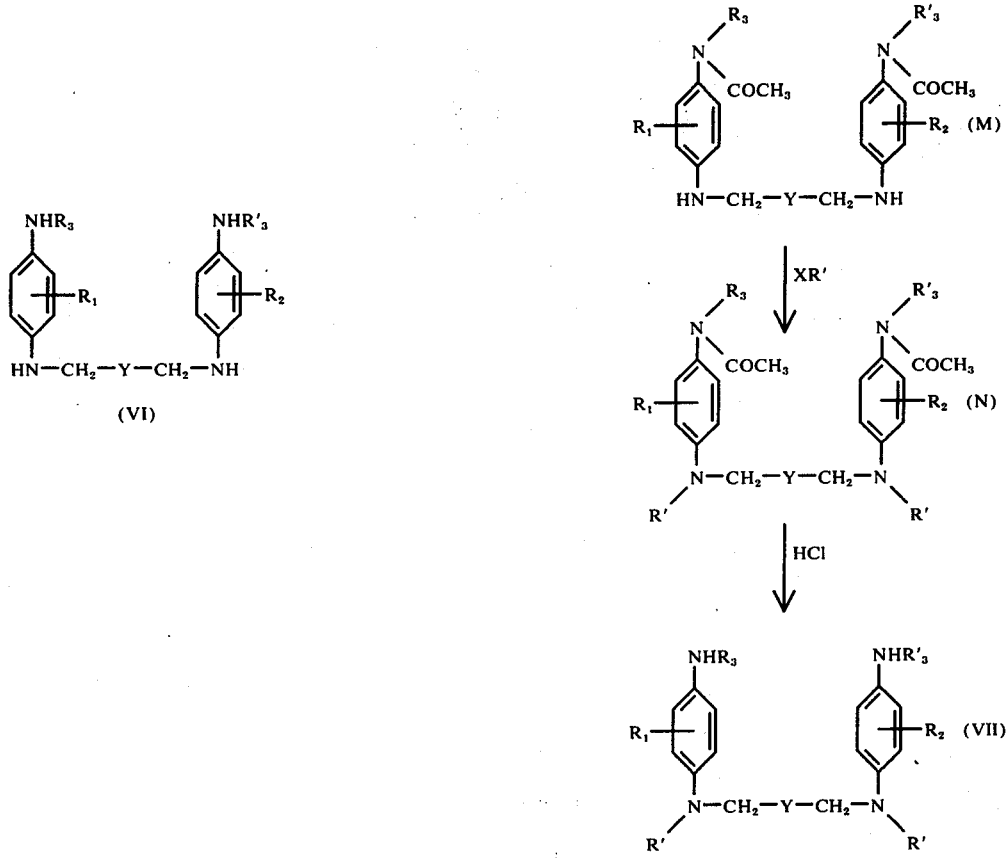

It is a further object of the present invention to provide a certain number of new chemical compounds which fall within general formula I. More specifically it is an object of the invention to provide as new articles of manufacture:

1. Those compounds of formula I in which the molecule is asymmetric, that is to say in which at least one of the two groups of substituents consisting of $R_1$ and $R_2$ on the one hand and $Z_1$ and $Z_2$ on the other hand consists of different radicals. In the following description these compounds are referred to as "asymmetric compounds".

2. Those compounds having the following formula Ia:

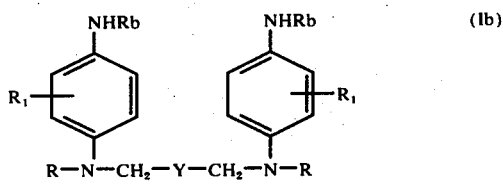

in which $R_1$ represents hydrogen, halogen or alkyl, and Ra represents aminoalkyl.

3. Those compounds having formula Ib:

in which R represents hydrogen, alkyl, hydroxy alkyl, or amino alkyl, in which the amino may be substituted, $R_1$ represents hydrogen, halogen or alkyl and Rb represents a lower alkyl.

The following examples illustrate different embodiments of the invention. These examples are given purely by way of illustration. The percentages are given by weight and temperatures in degrees Celsius.

EXAMPLES OF PREPARATION

EXAMPLE 1

Preparation of N,N'-bis-[(4-amino)phenyl]tetramethylene diamine tetrahydrochloride by means of the following reactions:

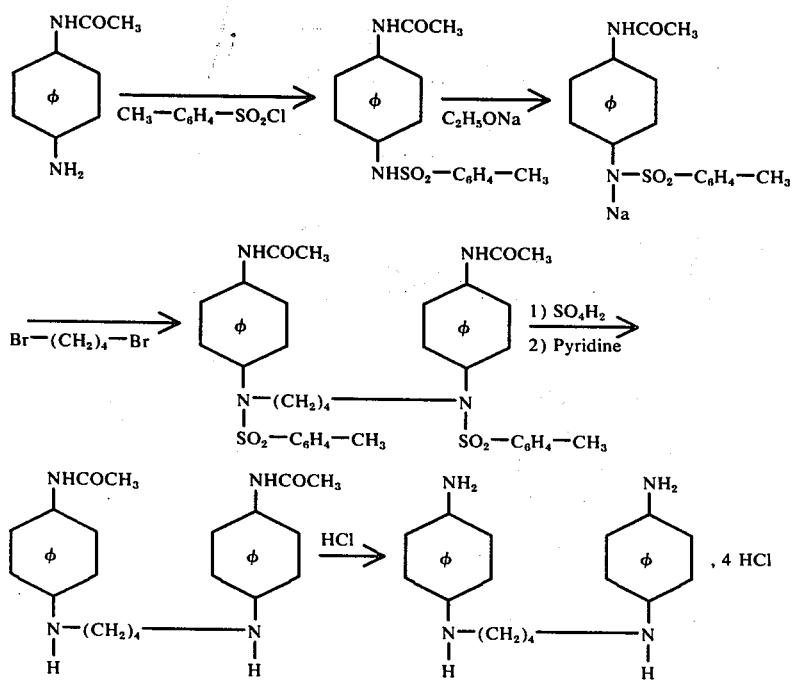

FIRST STEP

Preparation of 1-N-paratoluenesulfonylamino-4-acetylamino-benzene

A solution containing 297 g (1.92 mole) of para acetamino aniline in a liter of pyridine is mixed at between 30° and 40° with 475 g (2.5 mole) of paratoluene-sulfochloride. The reaction mixture is kept for 2 hours at 50°. It is then poured over 4 kg of cracked ice to which 500 cm³ of concentrated hydrochloric acid has been added. Drying yields 435 g of the crude product, which, after recrystallization in alcohol, melts at 184°.

SECOND STEP

Preparation of the sodium derivative of 1-N-paratoluene-sulfonylamino-4-acetylamino benzene 1.15 mole of the sulfonamide obtained in the first step are added to a solution of sodium ethylate obtained by adding 66g of sodium to 1750 cm³ of absolute alcohol. After heating this at reflux for half an hour, drying yields 375 g of the sodium derivative which is washed with a little hot absolute alcohol.

THIRD STEP

Preparation of N,N'bis-(paratoluenesulfonyl) N,N'-[(4-acetylamino)phenyl] tetramethylene diamine 24 cm³ (0.2 mole) of 1,4-dibromobutane are added slowly to a solution of 130 g (0.4 mole) of the sodium derivative obtained in the second step, which has first been heated to 95°, and mixed with 390 cm³ of dimethylformamide.

After the reaction mixture has been kept at 95° for an hour, it is poured into four liters of ice water, after which drying yields 90 g of the desired product which, after recrystallization in acetic acid, melts at 260°.

| Analysis | Calculated for $C_{34}H_{38}N_6O_6S_2$ | Found | |
|---|---|---|---|
| C % | 61.63 | 61.72 | |
| H % | 5.74 | 5.65 | |
| N % | 8.46 | 8.55 | 8.66 |
| S % | 9.66 | 9.60 | 9.80 |

FOURTH STEP

Preparation of N,N'bis-[(4-acetylamino) phenyl] tetramethylene diamine 84 g (0.12 mole) of N,N'-(paratoluenesulfonyl) N,N'-bis [(4-acetylamino) phenyl]tetramethylenediamine are dissolved in 330 cm³ of concentrated sulfuric acid at 0°. The reaction mixture is left to stand for 24 hours at the ambient temperature. It is then poured over 2 kg of ice. Drying yields the desired product in the form of a sulfate. This sulfate is treated with pyridine so as to produce 34.2 g of N,N'bis-[(4,acetylamino) phenyl] tetramethylenediamine which melts at 244°.

FIFTH STEP

Preparation of N,N'-bis [(4-amino) phenyl] tetramethylenediamine tetrahydrochloride 16 g (0.0454 mole) of N,N'-[(4-acetylamino)phenyl] tetramethylene diamine are added to 200 cm³ of concentrated hydrochloric acid and 100 cm³ of acetic acid. The reaction mixture is kept at reflux for 4 hours. After cooling, drying yields 17 g of N,N'bis-[(4-amino) phenyl] tetramethylene diamine tetrachlorhydride, which melts and decomposes at 245°.

| Analysis | Calculated for $C_{16}H_{26}N_4Cl_4$ | Found | |
|---|---|---|---|
| C % | 46.15 | 46.40 | 46.19 |
| H % | 6.25 | 6.40 | 6.35 |

-continued

| Analysis | Calculated for $C_{16}H_{26}N_4Cl_4$ | Found | | Analysis | Calculated for $C_{24}H_{34}N_4O_4$ | Found | |
|---|---|---|---|---|---|---|---|
| N % | 13.46 | 13.46 | 13.54 | C % | 65.16 | 65.22 | 65.05 |
|  |  |  |  | H % | 7.69 | 7.61 | 7.81 |
|  |  |  |  | N % | 12.67 | 12.72 | 12.90 |

EXAMPLE 2

Preparation of N,N'bis($\beta$-hydroxyethyl) N,N'bis-[(4-amino) phenyl] tetramethylene diamine tetrahydrochloride, according to the following process:

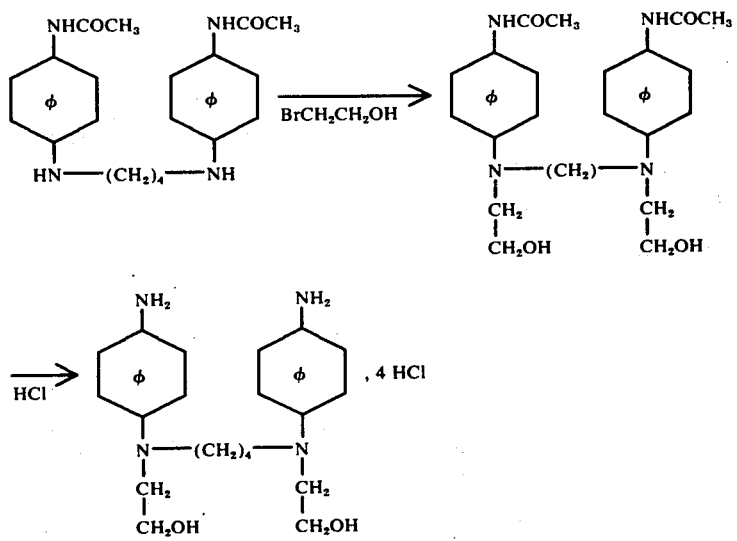

FIRST STEP

Preparation of N,N'bis-($\beta$-hydroxyethyl) N,N'-[(4-acetylamino) phenyl] tetramethylene diamine 4.5 g (0.0125 mole) of N,N'bis-[4-acetylamino-)phenyl] tetramethylenediamine are heated for 2 hours at 95° with 18 cm³ (0.1 mole) of 70% glycol hydrobromide, 9 cm³ of water and 5 g (0.05 mole) of calcium carbonate. This reaction mixture is poured into 100 cm³ of normal hydrochloric acid, and alkalized with ammonia. Drying yields 4.5 g of N,N'bis-($\beta$-hydroxyethyl) N,N'-[(4-acetylamino) phenyl] tetramethylene diamine which, after recrystallization in a dimethylformamide-water mixture, melts at 240°.

SECOND STEP

Preparation of N,N'bis-($\beta$-hydroxyethyl) N,N'[(4amino) phenyl] tetramethylene diamine tetrahydrochloride 30.6 g (0.0695 mole) of N,N'bis-($\beta$-hydroxyethyl) N,N'-[(4-acetylamino) phenyl] tetramethylene diamine are dissolved in 200 cm³ of concentrated hydrochloric acid and the reaction mixture is kept at reflux for an hour. It is then vacuum dried and the resulting crude product recrystallized with alcohol. The result is 34.5 g of N,N'bis-($\beta$-hydroxyethyl) N,N'bis-[(4-amino) phenyl] tetramethylene diamine tetrahydrochloride, which melts and decomposes at 230°.

EXAMPLE 3

Preparation of N,N'bis-[(4-methylamino) phenyl] tetramethylene diamine tetrahydrochloride, according to the following diagram:

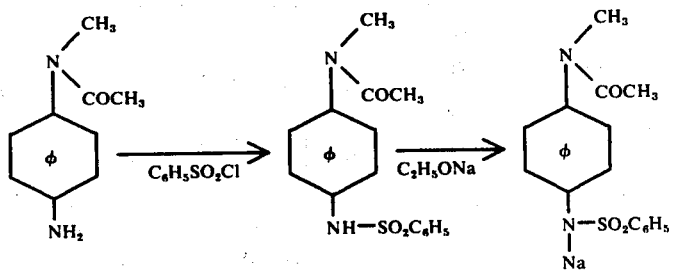

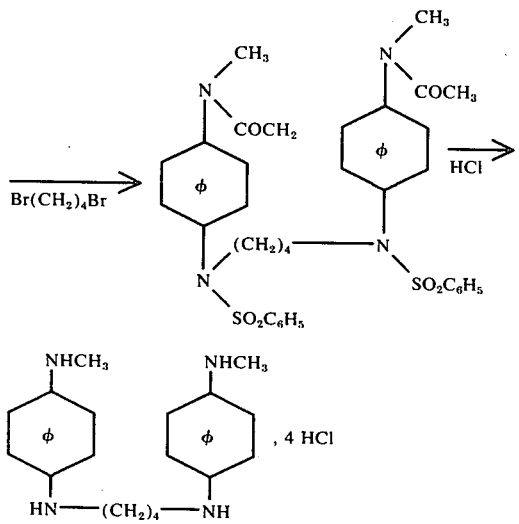

FIRST STEP

Preparation of 1-(N-methyl, N-acetyl)amino 4-N-benzenesulfonyl-amino benzene

This product is prepared by a process identical to the one described in the first step of Example 1, except that the paratoluenesulfochloride is replaced by benzene sulfochloride. After recrystallization in ethyl alcohol the product melts at 178.5°C.

SECOND STEP

Preparation of sodium derivative of 1-(N-methyl, N-acetyl)amino-4-N-benzene-sulfonylamino-benzene The sodium derivative is obtained by treating the sulfonamide prepared as above with an alcoholic solution of sodium ethylate following a procedure identical to the one described in the second step of Example 1.

THIRD STEP

Preparation of N,N'bis-[4-(methyl-acetylamino)phenyl]-N,N'bis-[(benzenesulfonyl)]tetramethylenediamine 1.3 cm³ (0.01 mole) of 1,4 dibromo butane are added slowly to a solution of 6.52 g (0.02 mole) of the sodium derivative described above in 20 cm³ of dimethylformamide, which has first been brought to 95°. After keeping the reaction mixture at 95° for an hour it is poured over 200 cm³ of ice water. Drying yields 6.1 g of the crude product which, after washing with a normal solution of NaOH and then with water is recrystallized in acetic acid. It melts at 235°.

FOURTH STEP

Preparation of N,N'bis-[4-(methylamino)phenyl] tetramethylenediamine tetrahydrochloride 3.5 g (0.0053 mole) of N,N'bis-[4(methyl-acetylamino)] phenyl N,N'bis-[(benzenesulfonyl)]tetramethylenediamine are added to 35 cm³ f concentrated hydrochloric acid and the reaction mixture is kept at reflux for 3 hours. After cooling, drying yields 2 g of N,N'bis-[4-(methylamino)phenyl] tetramethylenediamine tetrahydrochloride, which melts and decomposes between 228° and 230°.

Molecular weight calculated for $C_{18}H_{30}N_4Cl_4$ : 444

Molecular weight found by potentiometric measurement; 445.

EXAMPLE 4

Preparation of N-[(4-amino)phenyl] N'-[(4-amino-3-methyl)phenyl]N,N' ethylenediamine tetrahydrochloride in accordance with the following process:

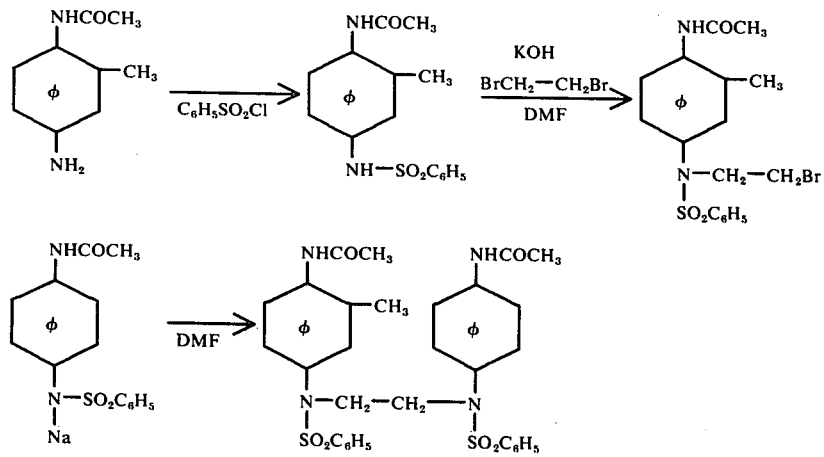

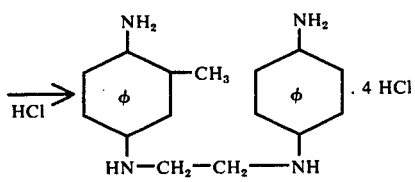

FIRST STEP

Preparation of 1-N-acetylamino-4-N-benzenesulfonylamino toluene 46.8 cm³ (0.366 mole) of benzenesulfochloride are added at between 40° and 50° to a solution containing 50 g (0.305 mole) of 1-acetylamino 4-amino toluene in 175 cm³ of pyridine. The reaction mixture is kept at this temperature for two hours and then poured over 700 g of cracked ice to which 40 cm³ of concentrated hydrochloric acid have been added. Drying yields 84 g of a crude product which, after recrystallization in alcohol, melts at 167°.

SECOND STEP

Preparation of 1-N-acetylamino-4[N-($\beta$-bromo-ethyl, N-benzenesulfonyl)]amino toluene 3.46 g (0.025 mole) of 85% potassium hydroxide in solution in 2 cm³ of water and 8 cm³ of absolute ethyl alcohol are added to a solution of 15.2 g (0.05 mole) of 1-acetylamino-N-benzenesulfonyl-4-amino-toluene in 60 cm³ of dimethylformamide. The reaction mixture is brought to 90° and 8.66 cm³ (0.1 mole) 1,4 dibromoethane are rapidly added. The mixture is heated in a boiling water bath for an hour. After cooling, 600 cm³ of ice water are added, and drying yields 13 g of the crude product. This is purified by washing it with a 2 N sodium hydroxide solution and then with water. After recrystallization in alcohol, it melts at 138.5°.

| Analysis | Calculated for $C_{17}H_{19}N_2O_3Br\,S$ | Found | |
|---|---|---|---|
| N % | 6.81 | 6.88 | 6.92 |
| S % | 7.78 | 7.89 | 7.85 |

THIRD STEP

Preparation of 1-N-acetylamino-4N-benzenesulfonylaminobenzene

This product is prepared by a process identical to the one described in the first step of Example 1 except that the paratoluenesulfochloride is replaced by benzenesulfochloride. After recrystallization in ethyl alcohol the products melts at 161°.

FOURTH STEP

Preparation of sodium derivative of 1-acetylamino-4-N-benzenesulfonyl-amino benzene This sodium derivative is obtained by treating the sulfonamide prepared as above with an alcoholic solution of sodium ethylate in a process identical to the one described in the second step of Example 1.

FIFTH STEP

Preparation of N[(4-acetylamino) phenyl] N'-[(4-acetylamino-3 methyl) phenyl] N,N'-(benzenesulfonyl) ethylenediamine 4.11 g (0.01 mole) of the brominated derivative prepared during the second step and 3.12 g (0.01 mole) of the sodium derivative prepared during the fourth step are dissolved in 35 cm³ of dimethylformamide at 120°. The reaction mixture is kept at this temperature for 2 hours. It is then cooled and 100 cm³ of water are added. Drying yields 5.5 g of the crude product which, after washing with a normal sodium hydroxide solution, and then with water, is recrystallized in acetic acid. It melts at 220°.

SIXTH STEP

Preparation of N[(4-amino) phenyl] N'-[(4-amino-3-methyl) phenyl] ethylene diamine tetrahydrochloride 5 g (0.008 mole) of N,N'-benzenesulfonyl N-[(4-acetylamino-) phenyl]N'-[(4-acetylamino-3 methyl) phenyl] ethylene diamine are added to 50 cm³ of concentrated hydrochloric acid and the reaction mixture is kept at reflux for 3 hours. After cooling, drying yields 2.3 g of the desired tetrahydrochloride, which melts and decomposes between 235° and 240°.

Molecular weight calculated: $C_{15}H_{24}N_4Cl_4$ : 402
Molecular weight found by potentiometric measurement: 398.

EXAMPLE 5

Preparation of N,N'bis-[$\beta$-(diethylamino) ethyl] N,N'bis-[(4-amino) phenyl] tetramethylenediamine tetrahydrochloride This compound is prepared by the following process:

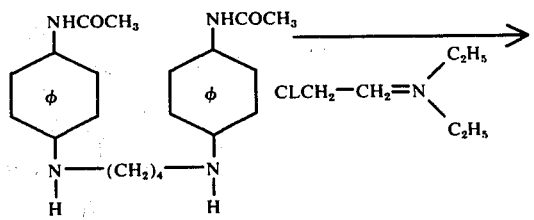

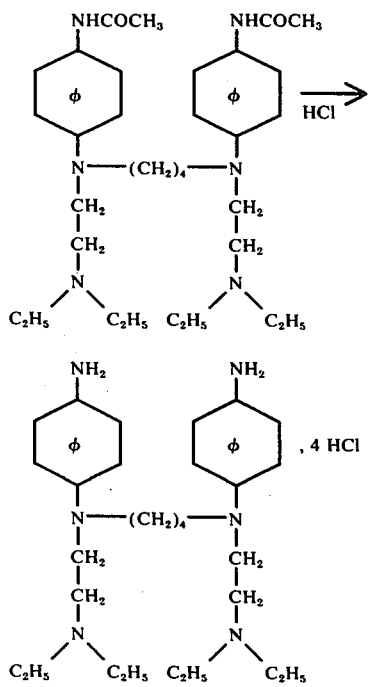

FIRST STEP

Preparation of N,N'bis-[β-(diethylamino) ethyl] N,N'bis-[(4-acetylamino) phenyl] tetramethylene diamine 0.85 mole (115 g) of diethylaminoethyl chloride is added little by little to a solution of 0.085 mole (30 g) of N,N'bis-[(4-acetylamino)]phenyl-tetramethylene diamine in 300 cm³ of nitrobenzene at 150°. The reaction mixture is kept at 150° for one hour. After cooling, drying yields the desired product in the form it its dihydrochloride. This crude dihydrochloride is treated with a normal sodium hydroxide solution and drying yields 28 g of N,N' [β-(diethylamino) ethyl] N,N'-[(4-acetylamino) phenyl] tetramethylene diamine which, after recrystallization in chlorobenzene, melts at 145°.

| Analysis | Calculated for $C_{32}H_{52}N_6O_2$ | Found | |
|---|---|---|---|
| C % | 69.56 | 69.24 | 69.46 |
| H % | 9.41 | 9.23 | 9.47 |
| N % | 15.21 | 15.12 | 15.33 |

SECOND STEP

Preparation of N,N'bis-[β(diethylamino) ethyl], N,N'bis-[4-amino phenyl] tetramethylene diamine tetrahydrochloride 0.05 mole (27.7 g) of N,N'bis-[β-(diethylamino) ethyl], N,N'bis[(4-acetylamino) phenyl] tetramethylenediamine is dissolved in 100 cm³ of concentrated hydrochloric acid and the reaction mixture is kept at reflux for three hours. It is then vacuum dried and the crude product thus obtained is recrystallized in a mixture of acetone and alcohol. This yields 27 g of N,N'λ bis-[ β -(diethylamino) ethyl ] N,N'bis-[(4-amino) phenyl] tetramethylenediamine tetrahydrochloride which melts and decomposes at 260°.

EXAMPLE 6

N-[(4-hydroxy) phenyl ] N'-[(4-amino) phenyl] ethylenediamine tetrahydrobromide

This compound is prepared by the following process:

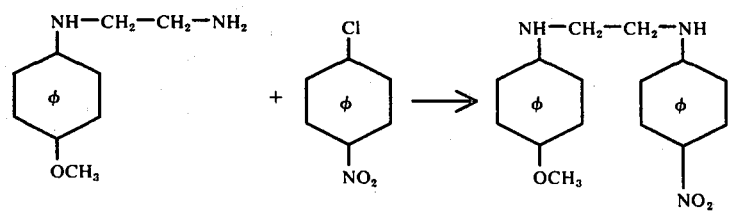

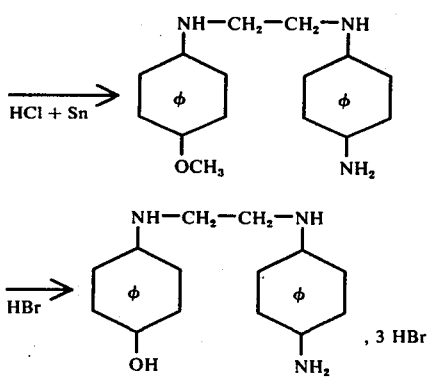

FIRST STEP

Preparation of N- [(4-methoxy) phenyl] N'-[(4-nitro) phenyl] ethylenediamine A mixture containing 0.1 mole (223 g) of N- β-aminoethyl paraanisidine and 0.447 mole (70.6 g) of parachloronitrobenzene is heated for 5 hours at 120°. After cooling the reaction mixture is poured into a liter of water and drying yields a crude product. This product after recrystallization in chlorobenzene, produces 80 g of N- [(4-methoxy) phenyl] - N'[4-nitro phenyl] ethylene diamine, which melts at 150°.

| Analysis | Calculated for $C_{15}H_{17}N_3O_3$ | Found | |
|---|---|---|---|
| C % | 62.72 | 62.50 | 62.53 |
| H % | 5.93 | 5.79 | 5.86 |
| N % | 14.63 | 14.51 | 14.68 |

SECOND STEP

Preparation of N-[(4-methoxy) phenyl]-N' [(4-amino) phenyl] ethylenediamine

The above nitro derivative is reduced in a conventional manner with hydrochloric acid and tin. After cooling, the reaction mixture, drying yields the desired product in the form of its hydrochloride. This is treated with a sodium hydroxide solution and yields N-[(4-methoxy) phenyl], N'[(4-amino) phenyl] ethylene diamine which melts at 58°.

| Analysis | Calculated for $C_{15}H_{17}N_3O_3$ | Found | |
|---|---|---|---|
| C % | 70.04 | 70.24 | 70.20 |
| H % | 7.39 | 7.61 | 7.60 |
| N % | 16.34 | 16.47 | 16.48 |

THIRD STEP

Preparation of N-[(4-hydroxy) phenyl], N'[(4-amino) phenyl] ethylenediamine trihydrobromide 0.233 mole (60 g) of N-[(4-methoxy) phenyl] N'-[(4-amino) phenyl] ethylenediamine is heated to reflux in 300 cm³ of 48% hydrobromic acid. After cooling the reaction mixture, drying yields 85 g of the trihydrobromide, which melts and decomposes at 280°.

| Analysis | Calculated for $C_{14}H_{17}N_3O$, 3 BrH | | Found |
|---|---|---|---|
| C % | 34.54 | 34.60 | 34.80 |
| H % | 4.11 | 4.23 | 4.09 |
| N % | 49.39 | 51.10 | 50.5 |

EXAMPLES OF COLORING COMPOSITIONS

EXAMPLE 1

The following solution is prepared:

| | |
|---|---|
| N,N'bis-[(4-amino) phenyl]tetramethylenediamine hydrochloride | 7 g |
| Metaaminophenol | 0.3 g |
| Resorcinol | 0.1 g |
| Metadiamino anisosulfate | 0.05 g |
| Aqueous ammonium lauryl sulfate solution, the concentration of which is 20% referred to lauryl alcohol | 20 g |
| Ethylene-diamino-tetracetic acid, sold under the trademark "TRILON B" | 0.3 g |
| 20% ammonia | 10 g |
| 40% sodium bisulfite | 1 g |
| Water, q.s.p. | 100 g |

This solution, when mixed with an equal weight of 6% hydrogen peroxide and applied for 30 minutes to 90% white hair, yields a deep ash blonde.

EXAMPLE 2

The following solution is prepared:

| | |
|---|---|
| N-[(4-amino) phenyl]N'-[(4-amino-3-methyl)phenyl] ethylene diamine tetrahydrochloride | 0.6 g |
| 2,4-diamino anisole | 0.65 g |
| Ammonium lauryl sulfate containing 40% lauryl alcohol | 20 g |
| Ethylene-diamino-tetraacetic acid sold under the trademark "TRILON B" | 0.3 g |
| 40% sodium bisulfite solution | 1 g |
| Ammonia at 22° Be | 10 g |
| Water, q.s.p. | 100 cc |

This solution, when mixed with an equal weight of 6% hydrogen peroxide and applied for 30 minutes to 100% white hair, produces a grayish blue.

EXAMPLE 3

| | |
|---|---|
| N,N'bis-[(4-methylamino) phenyl]tetramethylenediamine tetrahydrochloride | 1.11 g |
| 2,4-diamino anisole | 0.65 g |
| Ammonium lauryl sulfate containing 40% lauryl alcohol | 20 g |

-continued

| | |
|---|---|
| Ethylene-diamino-tetraacetic acid, sold under the trademark "TRILON B" | 0.3 g |
| 40% sodium bisulfite solution | 1 g |
| Ammonia at 22° Be | 10 g |
| Water, q.s.p. | 100 cm³ |

This solution, when mixed with an equal weight of 6% hydrogen peroxide and left for 30 minutes on 100% white hair, produces a slightly greenish gray.

EXAMPLE 4

The following solution is prepared:

| | |
|---|---|
| N-[(4-hydroxy)phenyl]-N'-[(4-amino) phenyl] ethylenediamino trihydrobromide | 10 g |
| Metadiaminoanisol sulfate | 0.5 g |
| Resorcinol | 0.1 g |
| Ammonium lauryl sulfate containing 20% lauryl alcohol | 20 g |
| Ethylene-diamino-tetraacetic acid sold under the trademark "TRILON B" | 0.3 g |
| 20% ammonia | 10 g |
| 40 % sodium bisulfite | 1 g |
| Water, q.s.p. | 100 g |

This solution when mixed with an equal weight of 6% hydrogen peroxide and left for 30 minutes on 80% white hair, produces a smoky blonde.

EXAMPLE 5

The following solution if prepared:

| | |
|---|---|
| N,N'bis-[(diethylamino) ethyl] N,N'bis-[(4-amino)-phenyl] tetramethylene diamine tetrahydrochloride | 6 g |
| Moradiamino anisol sulfate | 0.10 g |
| Resorcinol | 0.05 g |
| Ammonium lauryl sulfate containing 20% lauryl alcohol | 20 g |
| Ethylene-diamino-tetraacetic acid sold under the trademark "TRILON B" | 0.3 g |
| 20% ammonia | 10 g |
| 40% sodium bisulfite | 1 g |
| Water, q.s.p. | 100 g |

This solution, when mixed with an equal weight of 6% hydrogen peroxide, and applied for 30 minutes to 70% white hair, produces a steel gray.

What is claimed is:

1. A dye compound base for dyeing live human hair, said compound having the formula

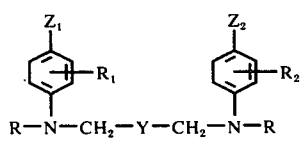

wherein $Z_1$ is selected from the group consisting of —$NH_2$, —$NHCH_3$ and —OH, $Z_2$ is selected from the group consisting of —$NH_2$ and —$NHCH_3$, $R_1$ and $R_2$ each independently are selected from the group consisting of hydrogen and methyl, R is selected from the group consisting of hydrogen, hydroxyethyl and diethylaminoethyl with R being diethylaminoethyl when $Z_1$ and $Z_2$ are both —$NH_2$ and Y is —$(CH_2)_n$— wherein $n$ is 0 or 2; and the salt of said compound with an acid selected from the group consisting of hydrochloric and hydrobromic acids.

2. A dye compound base for dyeing live human hair, said compound having the formula

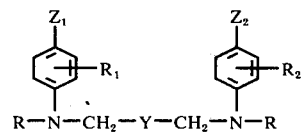

wherein $Z_1$ is selected from the group consisting of OH and $NHR_3$ wherein $R_3$ is selected from the group consisting of hydrogen and methyl, $Z_2$ is $NHR'_3$ wherein $R'_3$ is selected from the group consisting of hydrogen and methyl, $R_1$ and $R_2$ each independently are selected from the group consisting of hydrogen and methyl, R is selected from the group consisting of hydrogen, alkyl having 1–2 carbon atoms, hydroxy alkyl having 1–2 carbon atoms and amino alkyl having 1–2 carbon atoms and Y is —$(CH_2)_n$— wherein $n$ is 0–2; and the salt of said compound with an acid selected from the group consisting of hydrochloric acid and hydrobromic acid.

3. A dye compound base for dyeing live human hair, said compound having the formula

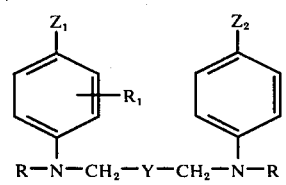

wherein $Z_1$ is selected from the group consisting of —OH, —$NH_2$ and —$NHCH_3$; $Z_2$ is selected from the group consisting of —$NH_2$ and —$NHCH_3$; $R_1$ is selected from the group consisting of hydrogen and $CH_3$; R is selected from the group consisting of hydrogen and diethylaminoethyl with R being diethylaminoethyl when $Z_1$ and $Z_2$ are both —$NH_2$; and Y is —$(CH_2)_n$ — wherein $n$ is 0 or 2; and the salt of said compound with an acid selected from the group consisting of hydrochloric and hydrobromic acid.

4. The dye compound of claim 3 which is N,N'-bis-[(4-methylamino)phenyl] tetramethylenediamine tetrahydrochloride.

5. The dye compound of claim 3 which is N,N'-[β-(diethylamino)ethyl]-N,N'-bis-[(4 amino)phenyl] tetramethylenediamine tetrahydrochloride.

6. The dye compound of claim 3 which is N-[(4-hydroxy)phenyl]-N'-[(4-amino)phenyl] ethylenediamine trihydrobromide.

* * * * *